United States Patent [19]

White et al.

[11] 4,126,683
[45] Nov. 21, 1978

[54] FUSED RING INDOLE DERIVATIVES AND ANTIDEPRESSANT COMPOSITIONS CONTAINING THEM

[75] Inventors: Alan C. White, Windsor; Robert F. Sugden, High Wycombe, both of England

[73] Assignee: John Wyeth & Brother Limited, Maidenhead, England

[21] Appl. No.: 804,648

[22] Filed: Jun. 8, 1977

[30] Foreign Application Priority Data

Jun. 11, 1976 [GB] United Kingdom ............... 24272/76

[51] Int. Cl.[2] .................. A61K 31/505; C07D 487/04
[52] U.S. Cl. ..................... 424/251; 544/252; 260/326.11 R; 424/273 R
[58] Field of Search ............... 260/251 A, 256.4 F; 424/251

[56] References Cited

U.S. PATENT DOCUMENTS

| | | | |
|---|---|---|---|
| 3,021,331 | 2/1962 | Lombardino et al. | 260/251 A |
| 3,542,782 | 11/1970 | Houlihan et al. | 260/251 A |
| 3,763,163 | 10/1973 | Hardtmann | 260/256.4 Q |
| 3,800,039 | 3/1974 | Marquis et al. | 424/251 |
| 3,850,957 | 11/1974 | White et al. | 260/309.6 |
| 3,891,644 | 6/1975 | White | 260/251 A |
| 3,957,819 | 5/1976 | White | 260/326.15 |
| 3,976,645 | 8/1976 | White | 260/251 A |

FOREIGN PATENT DOCUMENTS 1,366,133 9/1974 United Kingdom ............... 260/251 A

*Primary Examiner*—Donald G. Daus
*Assistant Examiner*—Diana G. Rivers
*Attorney, Agent, or Firm*—Arthur E. Wilfond

[57] ABSTRACT

The invention concerns novel fused ring indole derivatives of the formula

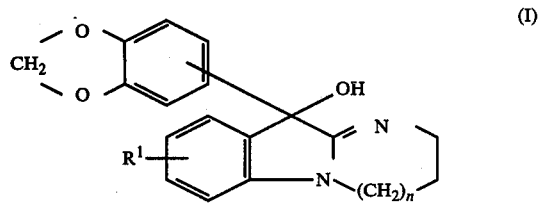

(I)

and the pharmaceutically acceptable acid addition and quaternary ammonium salts thereof, wherein n represents 1 or 2 and $R^1$ represents hydrogen, hydroxyl, lower alkyl, lower alkoxy, trifluoromethyl, halogen, amino or mono- or di-(lower)alkylamino. The compounds are useful as anti-depressant agents.

6 Claims, No Drawings

FUSED RING INDOLE DERIVATIVES AND ANTIDEPRESSANT COMPOSITIONS CONTAINING THEM

This invention relates to fused ring indole derivatives, to processes for their preparation and to pharmaceutical compositions containing them. The indole derivatives of this invention are derivatives of pyrimido [1,2-a]indoles and diazepino[1,2-a]indoles.

The present invention provides indole derivatives of general formula (I)

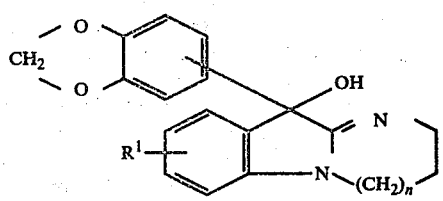
(I)

or pharmaceutically acceptable acid addition or quaternary ammonium salts thereof. In formula (I) $n$ represents 1 or 2 and $R^1$ represents hydrogen, hydroxyl, lower alkyl, lower alkoxy, trifluoromethyl, halogen, amino or mono-or di(lower)alkylamino.

The term "lower" as used herein means that the radical referred to contains 1 to 6 carbon atoms. Preferably such radicals contain 1 to 4 carbon atoms.

The compounds of the invention possess an asymmetric carbon atom and hence the compounds may be in the form of the optically active enantiomers or as mixtures of such enantiomers, e.g. racemates.

When $n$ is 1 the compounds are derivatives of pyrimido[1,2-a]indole and have the general formula (Ia)

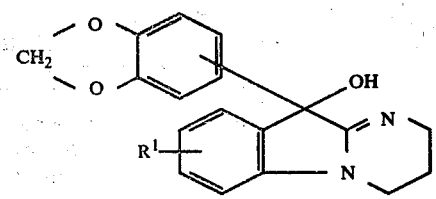
(Ia)

When $n$ is 2 the compounds are derivatives of diazepino[1,2-a]indoles and have the general formula (Ib)

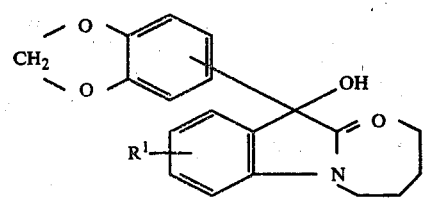
(Ib)

Preferably the compounds of the invention are those in which $n$ is 1, i.e. the compounds of general formula (Ia) and their pharmaceutically acceptable acid addition and quaternary ammonium salts.

Preferably in general formula (I), (Ia) and (Ib) the methylenedioxy group is attached to the 3,4-position of the phenyl ring.

$R^1$ can be hydrogen, hydroxyl, lower alkyl (e.g. methyl, ethyl, propyl, butyl), lower alkoxy (e.g. methoxy, ethoxy, propoxy, or butoxy), trifluoromethyl, halogen (e.g. chlorine or bromine), amino, mono(lower)alkylamino (e.g. methylamino) or di(lower)alkylamino (e.g. dimethylamino). Preferably $R^1$ is lower alkoxy or halogen or most preferably hydrogen.

The compounds of the invention may be prepared by reacting a ketone of general formula (II)

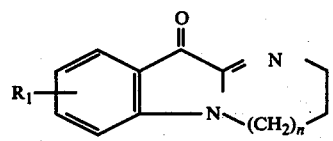
(II)

(where $n$ and $R^1$ have the meanings given above) with an organometallic reagent containing the organo group

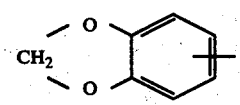

The organometallic compound is preferably, a Grignard reagent of formula

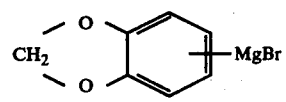

The reaction with the organometallic compound is generally carried out in an inert organic solvent, for example, ether or tetrahydrofuran, using, for example, conditions known for the particular reaction concerned. The ketone starting materials of general formula (II) and methods for their preparation are described in U.K. Patent Specification No. 1,366,133. The organometallic compounds are known compounds or can be prepared by methods described in the literature.

In an alternative process for preparing the compounds of the present invention an indole derivative of general formula

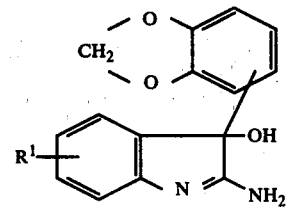
(III)

(where $R^1$ has the meanings given above) is condensed with a dihaloalkane of general formula (IV)

Hal.$(CH_2)_n(CH_2CH_2Hal'$  (IV)

wherein $n$ has the meaning defined above and Hal and Hal' are each chlorine, bromine or iodine.

The indole derivative of general formula (III) may exist in the alternative tautomeric form of general formula (IIIa)

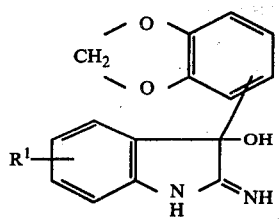

(IIIa)

and where, in the accompanying claims, there is used a formula implying any particular structure it is to be understood that the formula includes the alternative form or a mixture of such forms.

The reaction of the indole derivative and the dihaloalkane can be carried out in a manner analogous to that described in U.K. Patent Specification No. 1,427,066. The starting indole derivative can be prepared by a method similar to that for preparing analogous compounds described in U.K. specification No. 1,427,066. The dihaloalkanes or general formula (IV) are known compounds or can be prepared by methods described in the literature.

The compounds of the invention in which n is 1 may also be prepared by a process analogous to that described in the UK patent specification No. 1,450,137 i.e. cyclodehydration of a compound of general formula (V)

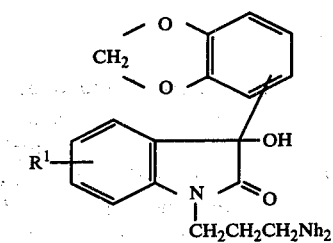

(V)

(where $R^1$ has the meaning given above). For further details of this process and for methods of preparing compounds analogous to those of general formula (V) reference is made to the above mentioned specification. Compounds of the invention in which n is 1 can also be made by a further process analogous to that described in U.K. Patent specification No. 1,450,543 i.e. cyclisation of an indole derivative of general formula (VI)

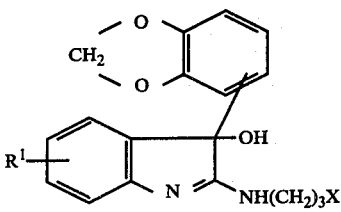

(VI)

(where $R^1$ has the meanings given above and X is a halogen atom). For further details of this process and for methods of preparing compounds analogous to those of general formula (VI) reference is made to the above mentioned U.K. Patent specification No, 1,450,543.

If any of the processes described above the compound of the invention is obtained as an acid addition salt, the free base can be obtained by basifying a solution of the acid addition salt. Conversely, if the product of any of the processes is a free base, a pharmaceutically acceptable acid addition salt may be obtained by dissolving the free base in a suitable organic solvent and treating the solution with an acid, in accordance with conventional procedures for preparing acid addition salts from base compounds. Examples of acid addition salts are those formed from inorganic acids and organic acids such as sulphuric, hydrochloric, hydrobromic, phosphoric, tartaric, fumaric, maleic, citric, acetic, formic, methanesulphonic and p-toluenesulphonic acids.

The compounds of general formula (I) are also capable of forming quaternary ammonium salts, and the invention also provides such salts. The quaternary salts may be prepared by treating the compound as its base in the presence or absence of a solvent, with an aryl-lower alkyl halide, lower alkyl halide, alkenyl halide, alkynyl halide or aminolower alkyl halide. Examples of such halides are methyl iodide and benzyl chloride and benzyl bromide.

The optical isomers of the compounds of formula (I) may be prepared by various processes. For example, a racemic mixture of a compound of the general formula (I) may be resolved by standard methods described in the literature such as by use of an optically active acid. The racemats may be prepared by any of the processes outlined above.

The compounds of the present invention possess pharmacological activity. In particular, they possess anti-depressant activity as indicated by standard pharmacological procedures. In one such procedure the compounds are tested for their ability to reverse the hypothermia produced by 2.5 mg/kg reserpine administered subcutaneously to mice (Askew, Life Sciences, 1963, 1, 725–730). In this procedure it was found that 10-(1,3-benzodioxol-5-yl)-2,3,4,10-tetrahydropyrimido[1,2-a] indol-10-ol, a representative compound of the present invention, produced a rise in rectal temperature, compared to the control, of 1.3° at 1 mg/kg, 3.3° at 4 mg/kg and 10.8° at 16 mg/kg. The dose to produce a rise of 8° is calculated at 9.5 mg/kg. The compound is a potent anti-depressant compound according to this procedure. For example, very few of the compounds specifically exemplified in U.K. Specification No. 1,366,133 produce a calculated rise in temperature of 8° C at dosages of less than 10 mg/kg. and hence the compound of the present invention is more active than most of the compounds of U.K. Specification No. 1,366,133.

The invention further provides a pharmaceutical composition which comprises a compound of general formula (I) or a pharmaceutically acceptable acid addition or quaternary ammonium salt thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavoring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pactin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; it if is too insoluble for this it can be dissolved in a suitable organic solvent, for instance aqueous propylene glycol containing from 10 to 75% of the glycol by weight is generally suitable.

In other instances compositions can be made by dispersing the finely-divided ingredient in aqueous starch or sodium carboxymethyl cellulose solution, or in a suitable oil, for instance arachis oil. Liquid pharmaceutical compositions which are sterile solutions or suspension can be utilised by intramuscular, iantraperitoneal or subcutaneous injection. In many instances a compound is orally active and can be administered orally either in liquid or solid composition form.

Preferably the pharmaceutically composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg, according to the particular need and the activity of the active ingredient. The invention also includes the compounds in the absence of carrier where the compounds are in unit dosage form. The daily dose of compound will vary depending upon the route of administration, the particular compound employed and the particular animal involved.

The following Examples illustrates the invention.

EXAMPLE 1

10-(1,3-Benzodioxol-5-yl)-2,3,4,10-tetrahydropyrimido [1,2-a]indol-10-ol (a) Magnesium (0.95 g.) was covered with dry tetrahydrofuran (12 ml) under dry nitrogen. Several drops of 5-bromobenzo-1,3-dioxole were added, followed by a few drops of 1,2-dibromoethane, and the mixture was warmed to start the reaction. Further neat 5-bromobenzo-1,3-dioxole (0.5 ml) was added, and the remainder (total 7.54 g) was diluted with dry tetrahydrofuran (25 ml) before being added dropwise to the gently refluxing reaction mixture. After the reaction subsided the mixture was heated at reflux for a further 30 mins.

(b) The solution from step (a) was triturated dropwise over 3½h at reflux with a solution of 3,4-dihydropyrimido [1,2-a]indol-10(2H)-one (4.64 g.) in dry tetrahydrofuran (250 ml) until a negative Gilman test was obtained. At this point 75% of the ketone solution had been added, indicating a 50% yield of Grignard reagent.

The mixture was cooled, treated with saturated aqueous ammonium chloride solution (50 ml), and evaporated under reduced pressure to remove tetrahydrofuran.

The residual aqueous phase was extracted with chloroform (4 × 50 ml) after filtration to remove a precipitated solid (0.85 g), shown to be a mixture of product and inorganic material, by IR and ignition. The combined extracts were dried (MgSO$_4$) and evaporated leaving a semi-crystalline material (5.96 g). Trituration with several portions of ether removed much oily material (1.8 g) and the residual solid was crystallised from acetonitrile, giving the impure base as brown prisms (2.89 g) mp 190°–192° C. The impure base was converted to its hydrochloride in methanol-ethereal HCl, and crystallised twice from methanol-ethyl acetate with charcoal treatment to give 10-(1,3-benzodioxol-5-yl)-2,3,4,10-tetrahydropyrimido[1,2-a]indol-10-ol monohydrochloride as colourless crystals (1.90 g) decomposing above 250° C, melting at 260°–265° C. Found: C, 62.7; H, 5.1; N, 8.1%. $C_{18}H_{16}N_2O_3 \cdot HCl$ requires C, 62.7; H, 5.0; N, 8.1%.

EXAMPLE 2

By following a procedure analogous to that of Example 1(a) but replacing 3,4-dihydropyrimido[1,2-a]indol-10(2H)-one with respectively (a) 8-chloro-3,4-dihydropyrimido[1,2-a]indol-10(2H)-one (U.K. Patent Specification No. 1,366,133)
(b) 3,4-dihydro-8-methoxypyrimido[1,2-a]indol-10(2H)-one (U.K. Patent Specification No. 1,366,133)
(c) 2,3,4,5-tetrahydro-1,3-diazepino[1,2-a]indol-11-one (U.K. Patent Specification No. 1.464,288)

there is obtained (a) 10-(1,3-benzodioxol-5-yl)-8-chloro-2,3,4,10-tetrahydropyrimido[1,2-a]indol-10-ol
(b) 10-(1,3-benzodioxol-5-yl)-8-methoxy-2,3,4,10-tetrahydropyrimido[1,2-a]indol-10-ol
(c) 11-(2,3-benzodioxol-5-yl)-2,4,5,11-tetrahydro-3H-1,3-diazepino[1,2-a]indol-11ol

We claim:

1. A compound selected from the group consisting of a fused ring indole derivative of formula

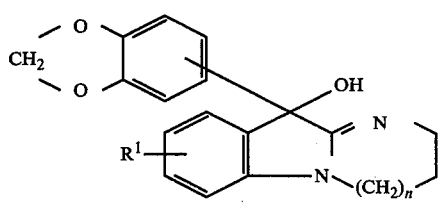

(I)

and a pharmaceutically acceptable acid addition or quaternary ammonium salt thereof wherein n represents 1 and $R^1$ represents hydrogen, hydroxyl, lower alkyl, lower alkoxy, trifluoromethyl, halogen, amino or mono- or di(lower)alkylamino.

2. A compound according to claim 1 wherein $R^1$ represents hydrogen, lower alkoxy or halogen 3. A compound according to claim 1 which is 10-(1,3-benzodioxol-5-yl)-2,3,4,10-tetrahydropyrimido [1,2-a]indol-10-ol or a pharmaceutically acceptable acid addition salt thereof.

4. A compound according to claim 1 which is 10-(1,3-benzodioxol-5-yl)-8-chloro-2,3,4,10-tetrahydropyrimido[1,2-a]indol-10-ol.

5. A compound according to claim 1 which is 10-(1,3-benzodioxol-5-yl)-8-methoxy-2,3,4,10-tetrahydropyrimido[1,2-a]indol-10-ol.

6. A pharmaceutical composition having antidepressant activity comprising an antidepressantly effective amount of a compound selected from the group consisting of a fused ring indole derivative of formula

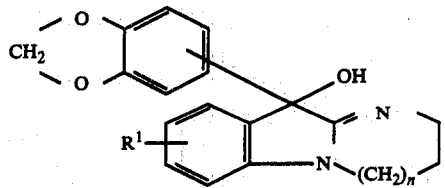

and a pharmaceutically acceptable acid addition or quaternary ammonium salt thereof wherein $n$ represents 1 and $R^1$ represents hydrogen, hydroxyl, lower alkyl, lower alkoxy, trifluoromethyl, halogen, amino or mono- or di(lower)alkylamino.

* * * * *